United States Patent [19]
Lacroix

[11] Patent Number: 5,913,901
[45] Date of Patent: Jun. 22, 1999

[54] ANKLE JOINT PROSTHESIS

[76] Inventor: Barry Lacroix, 866 Main Street East, Hamilton, ON, Canada, L8M 1L9

[21] Appl. No.: 09/084,186

[22] Filed: May 26, 1998

[51] Int. Cl.$^6$ ........................................................ A61F 2/66
[52] U.S. Cl. ................................................ 623/47; 623/53
[58] Field of Search .................................... 623/38, 47–53

[56] References Cited

U.S. PATENT DOCUMENTS

| | | | |
|---|---|---|---|
| 2,749,557 | 6/1956 | Riddle ........................................ | 623/50 |
| 4,413,360 | 11/1983 | Lamb et al. ............................... | 623/53 |
| 5,116,383 | 5/1992 | Shorter et al. ............................ | 623/49 |
| 5,156,630 | 10/1992 | Rappoport et al. ....................... | 623/47 |
| 5,800,564 | 9/1998 | Gelineau .................................... | 623/47 |

FOREIGN PATENT DOCUMENTS 330285  12/1970  Germany .................................. 623/38

*Primary Examiner*—Mickey Yu
*Assistant Examiner*—Bruce E. Snow

[57] ABSTRACT

The present invention is an ankle joint prosthesis which is used for connecting an artificial leg to an artificial foot wherein, said ankle joint prosthesis includes an upper ankle part which rigidly connects to the artificial leg and, a lower ankle part for rigidly connecting said ankle joint prosthesis to an artificial foot. The ankle joint prosthesis also includes a hollow shaft concentric with an ankle axis which is pivotally mounted in a shaft bore for rotating said upper and lower ankle parts relative to each other about the ankle axis. The ankle joint prosthesis also includes a locking mechanism having a semi-circular spine upper section with a radius centred about the ankle axis which is adapted to co-operate with and releasably mesh with splines on a semi-circular splined lower arc section. The ankle joint prosthesis also includes a plunger operably connected to said upper arc section, wherein depressing the plunger allows the wearer of the ankle joint prosthesis to self adjust the foot orientation using only finger pressure while said prosthesis is attached to said leg and foot and the plunger is operable by the wearer without disassembly of the prosthesis or the use of any additional aids or adjustment tools other than simple finger pressure.

12 Claims, 3 Drawing Sheets

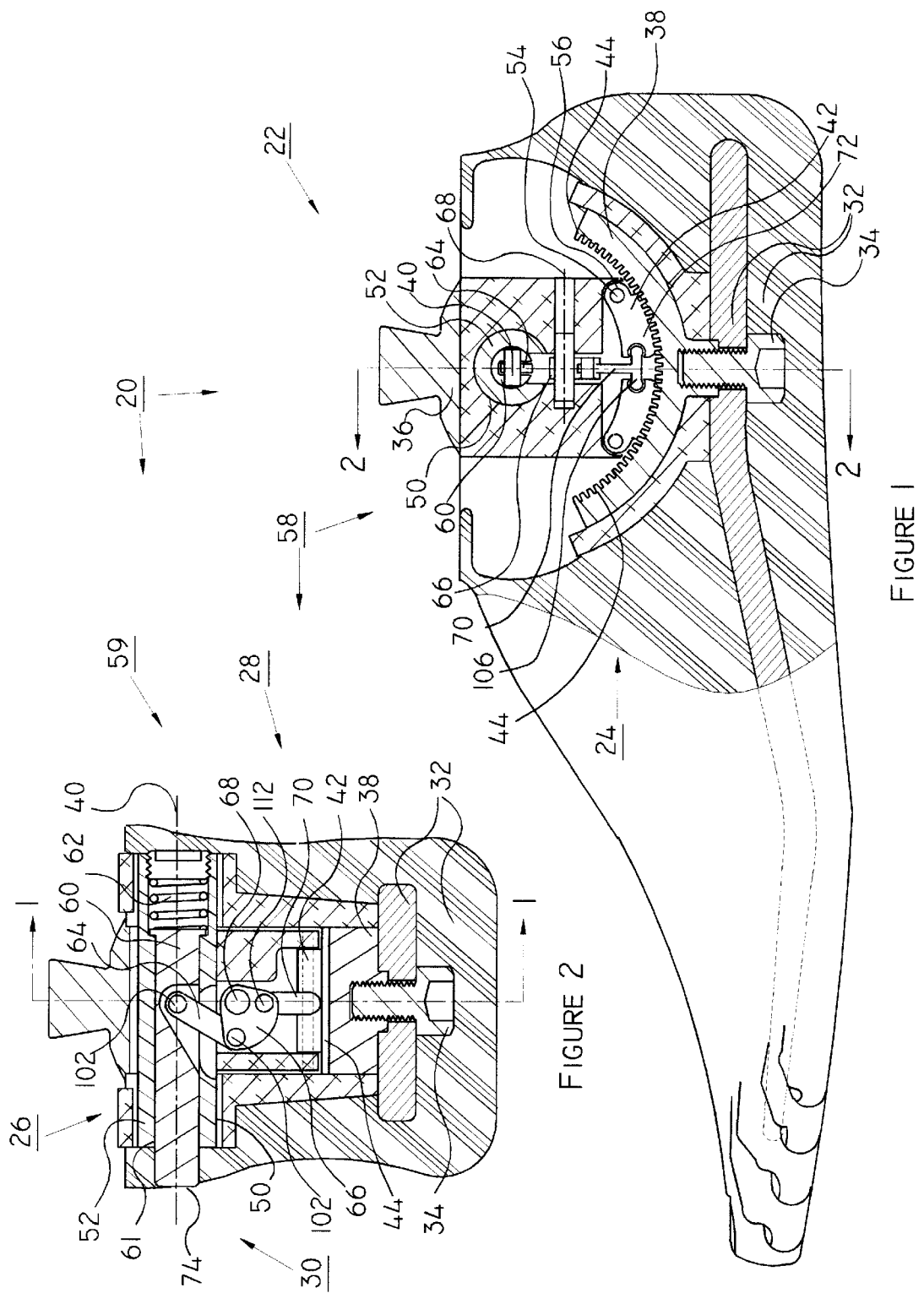

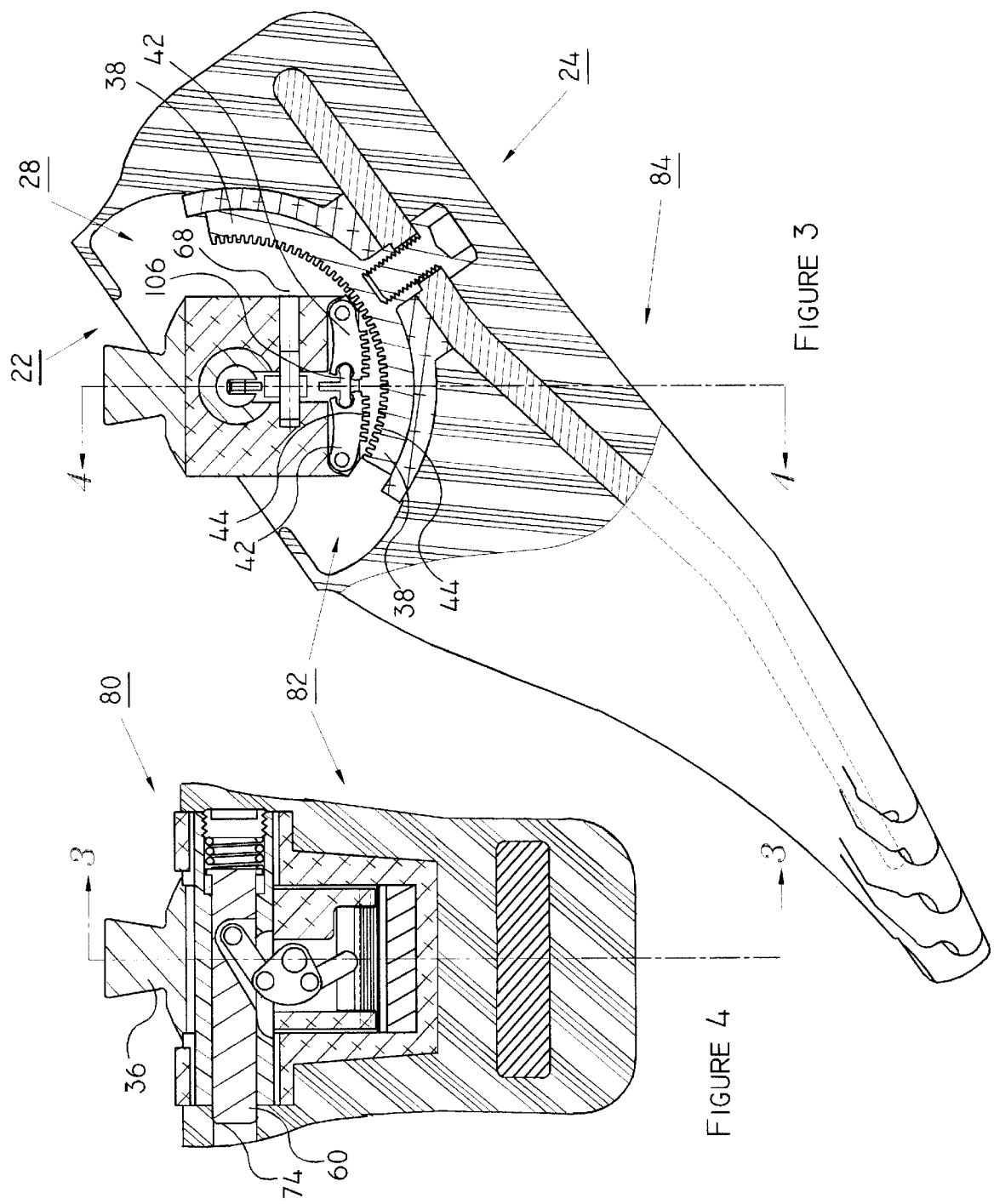

ANKLE JOINT PROSTHESIS

FIELD OF THE INVENTION

The present invention relates to a prosthetic ankle joint and more particularly to a ankle joint prosthesis having the ability to adjust an artificial foot in dorsi-flexion and/or planter flexion.

BACKGROUND OF THE INVENTION

Individuals who loose all or part of a leg have a residual limb to which a prosthetic foot is often attached using a mounting pylon. The attachment between the lower end of the pylon and the prosthetic foot approximates an ankle joint. However, in the past, pylons have been rigidly attached to prosthetic feet thus creating a rigid ankle joint. Rigid ankle joints have typically relied on the cushion in the heel of the prosthetic foot to allow relative axial motion between the residual limb and the ground. However, this approach has proven to be inadequate because it makes the individual walk awkwardly, and prone to stumble when standing on an incline.

The basic problem with the rigid ankle joint is that it does not mimic a real ankle. As a result, prosthetic designers have developed pivotal ankle joints. Such ankle joints may provide some motion in three potential orthogonal planes, namely the sagital, coronal, and transverse planes. The sagital plane is a vertical front-to-back plane and movement in the sagital plane is known as either dorsi-flexion in which the toe pivots upwardly or plantar flexion in which the toe pivots downwardly.

When an artificial foot is attached to an artificial limb, the initial alignment and adjustment fixes the heel height to a particular shoe and the user must continue to wear shoes that have identical heel heights. This often requires the amputee to wear the same model of shoe always. If a different shoe is worn the stability of the prosthesis is affected resulting in an unnatural gait and in some cases an unsafe limb. While the leg member can be subsequently disassembled, realigned and adjusted for a different heel height and again fitted to the user, this is a cumbersome process, and again the prosthesis is limited to a fixed prosthetic member.

The advantage of a prosthetic leg having a foot member with an adjustable heel height can be readily appreciated. The user can manually adjust the heel height of the foot member to an optimum position for comfort and safety for the particular shoes that he/she is wearing. The adjustment capability allows the amputee with minor training to self adjust for any heel height chose. The amputee is then afforded a wide variety of shoes from heelless slippers to high heel boots.

Accordingly, there is a need for an ankle joint prosthesis which allows self adjustment by the wearer of the heel height depending upon the shoes which are used in combination with the artificial foot and/or the terrain that the amputee is walking on.

SUMMARY OF THE INVENTION

The present invention an ankle joint prosthesis for connecting an artificial leg or stump with an artificial foot, said ankle joint prosthesis comprises an upper ankle part for rigidly connecting to said artificial leg or stump; a lower ankle part for rigidly connecting to said artificial foot; a means joining said upper ankle part with said lower ankle part, for rotating said upper and lower ankle parts relative each other about an ankle axis; a means for releasably locking rotational movement of said upper ankle part relative to said lower ankle part into pre-selected discreet orientations such that the ankle joint prosthesis can be selectively oriented in dorsi flexion or plantar flexion within plus or minus 70° relative to horizontal; said locking means includes a means for actuating said locking means between a locked position and an unlocked position using only finger pressure while said prosthesis is attached to said leg & foot, wherein said actuation means is operable by a wearer of said prosthesis without disassembly of the prosthesis or the use of any additional aids or adjustment tools other than simple finger pressure; and wherein said actuation means further includes a biasing means for maintaining said upper and lower ankle parts in a normally locked position preventing rotation of the ankle joint prosthesis.

Preferably said lower ankle part includes at least one semi-circular splined lower arc section with a radius centred about said ankle axis co-operating with said locking means, such that said locking means engages with said splines in a locked position and disengages from said splines in an unlocked position.

Preferably said locking means includes at least one semi-circular splined upper arc section with a radius centred about said ankle axis adapted to co-operate with and releasably mesh with said splines on said lower arc section, wherein urging said actuation means against the resistance of said biasing means moves said splined upper arc section between a normally locked position and an unlocked position, wherein said splines are meshed together in the locked position, and in the unlocked position said splines no longer mesh together wherein in said unlocked position said ankle parts are free to rotate relative each other, about said ankle axis.

Preferably said actuation means includes a plunger operably connected to said upper arc section, said plunger having a plunger actuation end which is exposed, accessible, and operable by the wearer, and wherein said plunger is slidably disposed in a plunger bore and is resiliently biased in an extended position by said biasing means, such that depressing the plunger with simple finger pressure slidably urges said plunger along said bore against said biasing means thereby urging said upper arc section from said normally locked position to said unlocked position.

Preferably said upper arc section pivots proximate a first end about an upper arc section pivot axis and a second end of said upper arc section is operably connected to the actuation means such that the biasing means normally biases said upper arc section against said lower arc section thereby meshing said splines in said normally locked position, wherein depressing said plunger pivots said upper arc section about said upper arc section pivot axis and away from said lower arc section to said unlocked position.

Preferably said actuation means further includes a rotatable bell crank pivoting about a bell crank pivot axis and operably connecting said plunger to said second end of said upper arc section, such that depressing said plunger rotates said bell crank and pivots said upper arc section from said locked position to said unlocked position.

Preferably said actuation means further includes a connecting rod pivotally connected at one end to said second end of said upper arc section and at the other end pivotally connected to said bell crank, and wherein said actuation means further includes a push rod pivotally connected at one end to said plunger and at the other end pivotally connected to said bell crank, such that depressing said plunger urges said push rod, which pivots said bell crank, which urges said connecting rod thereby urging said upper arc section from said normally locked position to said unlocked position.

Preferably said plunger bore is longitudinally aligned and concentric with said ankle axis.

Preferably said joining means includes a shaft longitudinally aligned and concentric with said ankle axis mounted in a shaft bore defined in said upper ankle part and said lower ankle part, such that said lower ankle part pivots about said shaft relative to said upper ankle part.

Preferably said joining means includes a hollow shaft longitudinally aligned and concentric with said ankle axis and pivotally mounted in a shaft bore defined in said upper ankle part and said lower ankle part such that said lower ankle part pivots about said hollow shaft relative to said upper ankle part, wherein said hollow portion of said shaft defines said plunger bore, such that a portion of said plunger is housed within said hollow shaft, and said plunger actuation end emerges and extends beyond said hollow shaft.

Preferably said biasing means is a coil spring housed within said plunger bore and biasing against said plunger to maintain an extended position, which corresponds to the locked position, whereas depressing said plunger compresses said coil spring thereby urging the upper arc section from said normally locked position to said unlocked position.

Preferably said splines in said upper and lower arc sections are adapted to allow 10 iterations of rotational movement about said ankle axis and between said upper ankle part relative to said lower ankle part, thereby releasably locking said upper and lower ankle parts in 10 increments of dorsi-flexion or planter flexion.

Preferably said locking means includes at least two semi-circular splined upper arc sections with a radii centred about said ankle axis, adapted to co-operate with and releasably mesh with said splines on said lower arc section, wherein urging said actuation means against the resistance of said biasing means moves said splined upper arc sections between a normally locked position and an unlocked position, wherein said splines are meshed together in the locked position, and in the unlocked position said splines no longer mesh together wherein in said unlocked position said ankle parts are free to rotate relative each other, about said ankle axis.

A method of self adjusting the orientation of an ankle joint prosthesis as described above comprises the steps of:

(a) wearing an ankle joint prosthesis as described above;

(b) actuating said actuation means of said ankle joint prosthesis as described above, thereby unlocking said locking means such that the upper and lower ankle parts are free to rotate relative each other;

(c) manually rotating said artificial foot into the desired orientation;

(d) releasing said actuation means thereby locking said foot into said desired orientation.

BRIEF DESCRIPTION OF THE DRAWINGS

The invention will now be described by way of example only, with references to the following drawings in which:

FIG. 1 is a side elevational cross-sectional schematic view of the ankle joint prosthesis mounted to an artificial foot and taken along line 1—1 of FIG. 2.

FIG. 2 is a rear cross-section elevational view showing the ankle joint prosthesis attached to an artificial foot, taken along line 2—2 of FIG. 1.

FIG. 3 is a side schematic elevational cross-sectional view taken along line 3—3 of FIG. 4 showing the ankle joint prosthesis in the unlocked position and rotated in planter flexion.

FIG. 4 is a rear elevational schematic view showing the ankle joint prosthesis mounted to artificial foot, the cross section taken along line 4—4 of FIG. 3.

DETAILED DESCRIPTION OF THE PREFERRED EMBODIMENT

Figure 5:
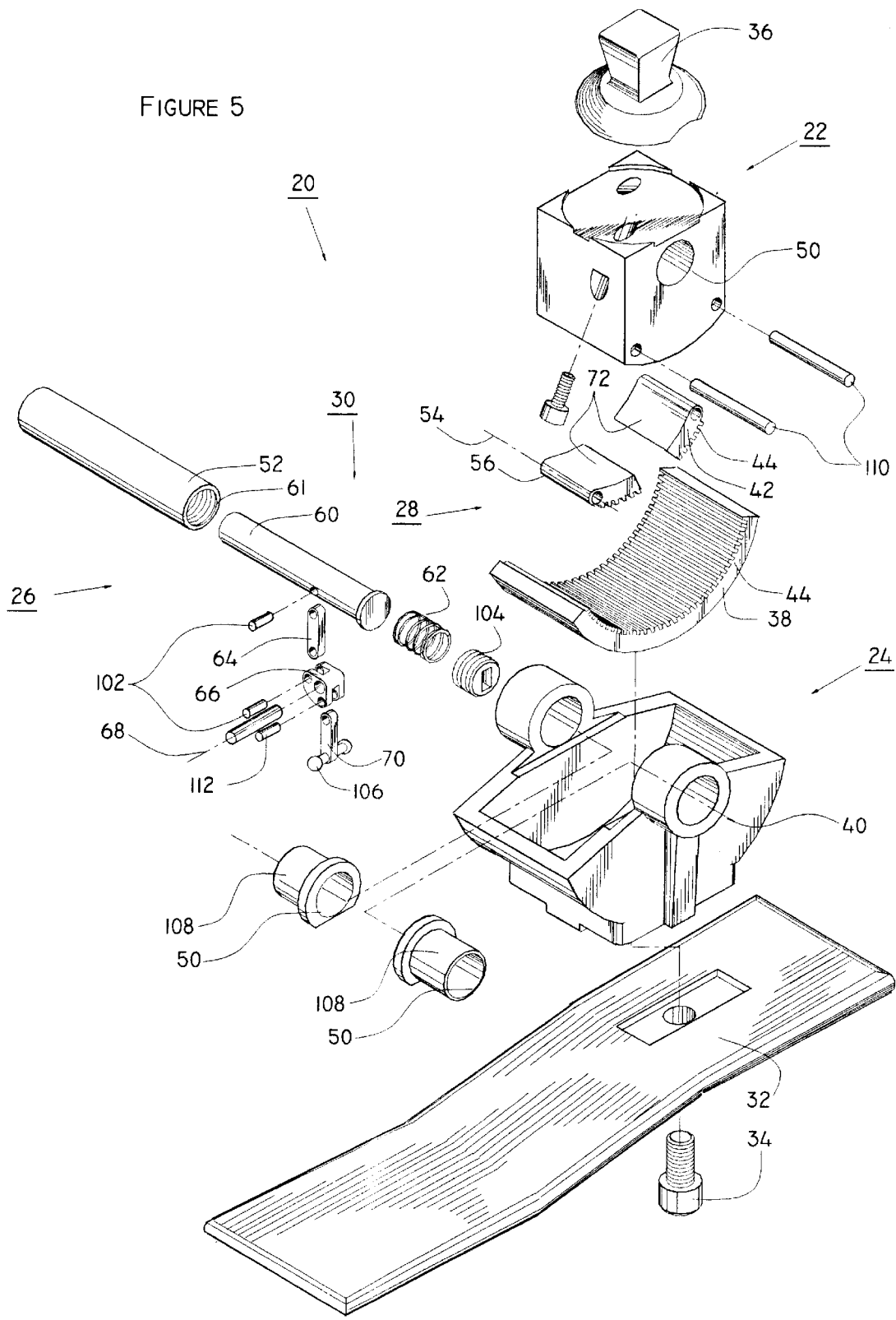
FIG. 5 is a schematic exploded view of the components of the ankle joint prosthesis including a portion of an artificial foot.

Referring now to FIGS. 1, 2 and 5 the present invention an ankle joint prosthesis is shown generally as 20 and includes the following major components: an upper ankle part 22, a lower ankle part 24, a joining means shown generally as 26, a locking means shown generally as 28, and an actuation means shown generally as 30. Referring to FIGS. 1 and 2, lower ankle part shown generally as 24 is shown connected to an artificial foot 32. Artificial foot 32 is not part of the present invention, however, artificial foot 32 is shown in FIGS. 1 and 2 as an example of how the present ankle joint prosthesis 20 can be connected to an artificial foot 32. Ankle joint prosthesis 20 can be adapted to be rigidly connected to almost any type of artificial foot that is currently available on the market and the FIG. 1 illustration showing the connection between lower ankle part 24 and artificial foot 32 is for illustrative purposes only.

In addition, upper ankle part 22 is shown with an inverted pyramid 36 pylon attachment point which is a standard attachment type arrangement used with leg prosthesis. An artificial leg not shown would be connected to inverted pyramid 36 in the conventional manner known in the art of artificial limbs. Inverted pyramid 36 is shown for illustrative purposes only and any other kind of connection or pylon between upper ankle part 22 and a artificial leg can be used, however, inverted pyramid 36 is shown in FIG. 1 for illustrative purposes.

Referring now to FIGS. 1, 2 and 5 joining means shown generally as 26 includes a shaft bore 50 passing through upper ankle part 22 as well as lower ankle part 24 wherein said shaft bore 50 is concentrically aligned with ankle axis 40. Lower ankle part 24 and upper ankle part 22 are aligned such that a hollow shaft 52 is received within shaft bore 50 such that lower ankle part 24 can pivot relative to upper ankle part 22 about ankle axis 40.

Referring now to FIGS. 1, 2, 3, 4 and 5 locking means shown generally as 28 includes a semi-circular splined lower arc section 38 such that the semi-circular arc section 38 has a radius centred about an ankle axis 40. Locking means 28 further includes a semi-circular splined upper arc sections shown as 42 which also have radius centred about ankle axis 40 such that the splines 44 on lower arc section 38 co-operate with and mesh with splines 44 on upper arc section 42 preventing upper ankle part 22 from pivoting relative to lower ankle pair 24, when in a locked position 58.

Locking means 28 includes two upper arc sections 42, each having an upper arc section pivot axis 54 located at a first end 56 of upper arc section 42 such that downwardly pivoting upper arc section 42 about upper arc section pivot axis 54 toward lower arc section 38 meshes splines 44 on upper arc section 42 with splines 44 on lower arc section 38 thereby preventing pivoting of upper ankle part 22 relative to lower ankle part 24 about ankle axis 40. Pivoting upper arc section 42 about upper arc section pivot axis 54 upwardly away from lower arc section 38 separates splines 44 thereby allowing upper ankle part 22 to pivot relative to lower ankle part 24. When splines 44 of upper arc section 42 are meshed with splines 44 of lower arc section 38 the locking means 28 is in a locked position 58 shown in FIG. 1 and 2. Pivoting upper arc section 42 away from lower arc section 38 separating splines 44 from lower arc section 38 renders the locking means 28 is in an unlocked position 82 as shown in FIGS. 3 and 4. In the unlocked position 82, upper ankle part 22 is free to rotate relative to lower ankle part 24 about ankle axis 40 since hollow shaft 52 allows pivoting of upper ankle part 22 relative to lower ankle part 24.

The actuation means shown generally as 30 includes a plunger 60, a plunger bore 61, spring 62, push rod 64, bell crank 66, bell crank pivot axis 68, connecting rod 70 and second end 72. Plunger 60 shown in an extended position 59 in FIGS. 1 & 2, is partially received within plunger bore 61 which is longitudinally aligned and concentric with ankle axis 40. Plunger 60 is received concentrically within plunger bore 61 within hollow shaft 52. Thereby plunger 60 and hollow shaft 52 are both concentrically aligned along ankle axis 40.

Spring 62 is also located within plunger bore 61 and abuts against plunger 60 biasing against plunger 60 to maintain plunger 60 in an extended position 59 which corresponds with locked position 58. In other words when plunger 60 is in the extended position 59, upper arc sections 42 are in the locked position 58. Plunger 60 also has a plunger actuation end 74 which extends beyond hollow shaft 52 in order for the wearer of the ankle joint prosthesis 20 to simply apply finger pressure on plunger actuation end 74 thereby urging plunger 60 slidably along plunger bore 61 against the bias of spring 62. Depressing plunger 60 into a retracted position 80 operably moves upper arc section to the unlocked position 82 as shown in FIGS. 3 and 4.

Pivotally connected to plunger 60 is push rod 64 as shown the Figures. Note that hollow shaft 52 requires the necessary relief to allow push rod 64 to pass through a section of hollow shaft 52. As shown, push rod 64 is connected pivotally at one end to plunger 60 and pivotally at the other end to bell crank 66. Bell crank 66 pivots about bell crank pivot axis 68. Connecting rod 70 is pivotally connected at one end to bell crank 66 and at the other end is pivotally connected to a second end 72 of upper arc section 42.

In use ankle joint prosthesis 20 is rigidly attached to an artificial leg by using the inverted pyramid 36 pylon or other the methods known in the art of artificial limbs for attaching prosthesis together. The inverted pyramid 36 is shown on upper ankle part 22 by way of illustration only and any other means of connecting upper ankle part to an artificial leg which is known in the art can be utilized to join ankle joint prosthesis 20 to an artificial leg.

Secondly lower ankle part 24 is rigidly connected to an artificial foot 32 as illustrated in FIGS. 1 and 2. Artificial foot 32 is rigidly connected to lower ankle part 24 with bolt 34 as shown in the Figures. Any other method of connecting lower ankle pair to artificial foot 32 known in the art can be used. The present method of attaching artificial foot 32 to lower ankle part 24 is shown by way of example only. Artificial foot 32 is only one possible type of foot that may be used with the present invention.

Plunger 60 as shown in FIGS. 1 and 2 is in an extended position 59 which corresponds with a locked position 58 of upper arc section 42. When plunger 60 is in extended position 59, the splines 44 of upper arc section 42 and lower arc section 38 mesh together thereby preventing relative movement of upper ankle part 22 and lower ankle part 24 about shaft 52 which is concentric about ankle axis 40. This locked position 58 is normally maintained by the bias of spring 62 against plunger 60.

In order to unlock and allow relative rotation between lower ankle part 24 and upper ankle part 22, the wearer of the ankle joint prosthesis simply needs to apply finger pressure to plunger actuation end 74 thereby urging plunger 60 against the bias of spring 62 and moving plunger 60 longitudinally along plunger bore 61, to a retracted position 80 which corresponds to unlocked position 82, shown in FIGS. 3 and 4.

Moving plunger 60 along plunger bore 61 urges push rod 52 which is pivotally connected to bell crank 66 thereby rotating bell crank 66 about bell crank pivot axis 68. Rotation of bell crank 66 in turn urges connecting rod 70 upwardly thereby urging second end of upper arc section 42 upwardly by pivoting upper arc section 42 about upper arc section pivot axis 54 thereby separating splines 44 of upper arc section 42 and lower arc section 38 putting the ankle joint prosthesis into the unlocked position 82. In the unlocked position 82, the splines 44 of upper arc section 42 and lower arc section 38 are no longer meshed together, allowing upper and lower ankle parts 22 and 24 to pivot relative each other.

Referring now to FIG. 5, which is an exploded view of the present invention the ankle joint prosthesis 20 is shown together with a portion of an artificial foot 32 which is attached to lower ankle part 24 with bolt 34. In this exploded view, one can also readily see push rod pins 102 which attach the push rod to plunger 60 at one end and to bell crank 66 at the other end. One can also see connecting rod pin 112 which connects, connecting rod 70 to bell crank 66 at one end and also the wrist pin 106 which cooperates with the second end 72 of upper arc sections 42 in order to pivot upper arc sections 42 about upper arc section pins 10 shown as in FIG. 5. As well a spring stop 104 is illustrated in FIG. 5 which is threadably received within hollow shaft 52 in order to retain spring 62 in its proper position. In addition, exploded view FIG. 5 also illustrates the use of bearings shown as 108 which in this case are shown as bush type bearings which can be used in order to better support hollow shaft 52 along ankle axis 40. Lower ankle part 24 is modified accordingly in order to receive bearings 108 along ankle axis 40.

Referring now to FIG. 3 the foot is shown rotated from a normal horizontal position into a plantar flexion position 84 and as well locking means 28 is shown in the unlocked position 82 which corresponds to plunger 60 in the retracted position 80. It will be apparent to those skilled in the art that the foot can be rotated and locked into any dorsi-flexion position or any plantar flexion position between 0 and 80 from the normal horizontal position. Thereby, the heel of the foot can be lifted or lowered depending upon the shoe which the wearer of the prosthesis is currently using.

It will also be apparent to those skilled in the art that there can be any number of upper arc sections, preferably, however there are two as shown in the attached diagrams, however, the ankle joint prosthesis 20 will work equally well with only one or more upper arc sections 42. The spacing of splines 44 will determine the incremental rotation of the foot, however, preferably the splines will allow 1° increments of either dorsi-flexion or plantar flexion for the wearer of this prosthesis.

It will be apparent to those skilled in the art that the spacing of the splines will also be determined by the strength requirements of the splines and the forces applied to the foot as well as the fineness in adjustment required for a particular user of the ankle joint prosthesis 20.

Using the present ankle joint prosthesis 20 allows the wearer to be able to quickly self adjust the heel height of the artificial foot by simply using finger pressure to depress the plunger actuation end 74. Depressing plunger 60 from an extended position 59 to a retracted position 80 unlocking locking means 28 allows the user to manually tilt the foot until the desired heel height and/or foot orientation is obtained. It is desirable for a person having an artificial leg and/or foot to be able to self adjust the heel height quickly in order to accommodate the differences in heel height when going from a flat shoe for example, to a raised heel or a dress shoe.

It should be apparent to persons skilled in the arts that various modifications and adaptations of this structure described above are possible without departure from the spirit of the invention the scope of which defined in the appended claims.

I claim:

1. An ankle joint prosthesis for connecting an artificial leg or stump with an artificial foot, said ankle joint prosthesis comprising:

(a) an upper ankle part for rigidly connecting to said artificial leg or stump;

(b) a lower ankle part for rigidly connecting to said artifical foot;

(c) a means joining said upper ankle part with said lower ankle part, for rotating said upper and lower ankle parts relative each other about an ankle axis;

(d) a means for releasably locking rotational movement of said upper ankle part relative to said lower ankle part into pre-selected discreet orientations such that the ankle joint prosthesis can be selectively oriented in dorsi flexion or plantar flexion relative to horizontal;

(e) said locking means includes a means for actuating said locking means between a locked position and an unlocked position uising only finger pressure while said prosthesis is attached to said leg & foot, wherein said actuation means is operable by a wearer of said prosthesis without disassambly of the prosthesis or the use of any additional sides or adjustment tools other than simple finger pressure;

(f) a biasing means for maintaining said locking means in a normally locked position preventing rotation fo the ankle joint prosthesis, (g) wherein said lower ankle part includes at least one semi-circular splined lower arc section with a radius centered about said ankle axis co-operating with said locking means, such that said locking means engages with said splines in a locked position and disengages from said splines in an unlocked position; and (h) wherein said locking means includes at least one semi-circular splined upper arc section with a radius centred about said ankle axis adapted to co-operate with and releasably mesh with said splines on said lower arc section, wherein urging said actuation means against the resistance of said biasing means moves said splined upper arc section between a normally locked position and an unlocked position, wherein said splines are meshed together in the locked position, and in the unlocked position said splines no longer mesh together wherein in said unlocked position said ankle parts are free to rotate relative each other, about said ankle axis.

2. The ankle joint prosthesis in claim 1, wherein said actuation means includes a plunger operably connected to said upper arc section, said plunger having a plunger actuation end which is exposed, accessible, and operable by the wearer, and wherein said plunger is slidably disposed in a plunger bore and is resiliently biased in an extended position by said biasing means, such that depressing the plunger with simple finger pressure slidably urges said plunger along said bore against said biasing means thereby urging said upper arc section from said normally locked position to said unlocked position.

3. The ankle joint prosthesis claimed in claim 2, wherein said upper arc section pivots proximate a first end about an upper arc section pivot axis and a second end of said upper arc section is operably connected to the actuation means such that the biasing means normally biases said upper arc section against said lower arc section thereby meshing said splines in said normally locked position, wherein depressing said plunger pivots said upper arc section about said upper arc section pivot axis and away from said lower arc section to said unlocked position.

4. The ankle joint prosthesis in claim 3, wherein said actuation means further includes a rotatable bell crank pivoting about a bell crank pivot axis and operably connecting said plunger to said second end of said upper arc section, such that depressing said plunger rotates said bell crank and pivots said upper arc section from said locked position to said unlocked position.

5. The ankle joint prosthesis in claim 4, wherein said actuation means further includes a connecting rod pivotally connected at one end to said second end of said upper arc section and at the other end pivotally connected to said bell crank, and wherein said actuation means further includes a push rod pivotally connected at one end to said plunger and at the other end pivotally connected to said bell crank, such that depressing said plunger urges said push rod, which pivots said bell crank, which urges said connecting rod thereby urging said upper arc section from said normally locked position to said unlocked position.

6. The ankle joint prosthesis in claim 2, wherein said plunger bore is longitudinally aligned and concentric with said ankle axis.

7. The ankle joint prosthesis in claim 2, wherein said joining means includes a hollow shaft longitudinally aligned and concentric with said ankle axis and pivotally mounted in a shaft bore defined in said upper ankle part and said lower ankle part such that said lower ankle part pivots about said hollow shaft relative to said upper ankle part, wherein said hollow portion of said shaft defines said plunger bore, such that a portion of said plunger is housed within said hollow shaft, and said plunger actuation end emerges and extends beyond said hollow shaft.

8. The ankle joint prosthesis in claim 7, wherein said biasing means is a coil spring housed within said plunger bore and biasing against said plunger to maintain an extended position, which corresponds to the locked position, whereas depressing said plunger compresses said coil spring thereby urging the upper arc section from said normally locked position to said unlocked position.

9. The ankle joint prosthesis claimed in claim 1 wherein said splines in said upper and lower arc sections are adapted to allow 1° iterations of rotational movement about said ankle axis and betwen said upper ankle part relativet to said lower ankle part, thereby releasable locking said upper and lower ankle parts in 1° increments of dorsi-flexion or plantar flexion.

10. The ankle joint prosthesis claimed in claim 1 wherein said locking means includes at least two semi-circular splined upper arc sections with a radii centred about said ankle axis, adapted to co-operate with and releasably mesh with said splines on said lower arc section, wherein urging said actuation means against the resistance of said biasing means moves said splined upper arc sections between a normally locked position and an unlocked position, wherein said splines are meshed together in the locked position, and in the unlocked position said splines no longer mesh together wherein in said unlocked position said ankle parts are free to rotate relative each other, about said ankle axis.

11. An ankle joint prosthesis for connecting an artificial leg or stump with an aritificial foot, said ankle joint prosthesis comprising:

(a) an upper ankle part for rigidly connecting to said artificial leg or stump;

(b) a lower ankle part for rigidly connecting to said artificial foot;

(c) a hollow shaft joining said upper ankle part with said lower ankle part, for rotating said upper and lower ankle parts relative each other about an ankle axis;

(d) a locking means for releasably locking rotational movement of said upper ankle part relative to said lower ankle part into pre-selected discreet orientations such that the ankle joint prosthesis can be selectively oriented in dorsi flexion or plantar felxion within plus or minus 70° relative to horizontal, said locking means including at least one semi-circular splined lover arc section with a radius centred about said ankle axis, and at least one semi-circular splined upper arc section with a radius centred about said ankle axis adapted to co-operate with and releasably engages and meshes with said splines on said lower arc seciton such that said locking means engages said splines in a locked position and disengages said splines in an unlocked position and, said splined upper arc sections moveable between a normally locked position and an unlocked position, wherein said splines are meshed together in the locked position, and in the unlocked position said splines no longer mesh together wherein said said unlocked position said ankle parts are free to rotate relative each other about said ankle axis;

(e) a plunger for actuating said locking means, said plunger operably connected to said upper arc sections, wherein only finger pressure is required to depress the plunger while said prosthesis is attached to said leg & foot, wherein said plunger is operable by a wearer of said prosthesis without disassembly of the prosthesis or the use of any additional aids or adjustment tools other than simple finger pressure; and (f) a spring for maintaining said locking means in a normally locked position preventing rotation of the ankle joint prosthesis.

12. A method of self adjusting the orientation of an ankle joint prosthesis comprising the steps of:

(a) wearing an ankle joint prosthesis as claimed in claim 4;

(b) actuating said actuation means of said ankle joint prosthesis claimed in claim 4, thereby unlocking said locking means such that the upper and lower ankle parts are free to rotate relative each other;

(c) manually rotating said artificial foot into the desired orientation;

(d) releasing said actuation means thereby locking said foot into said desired orientation.

* * * * *